United States Patent [19]

Powell et al.

[11] Patent Number: Plant 5,339

[45] Date of Patent: Nov. 13, 1984

[54] DWARF AUSTRALIAN TREE FERN

[75] Inventors: David A. Powell; Salvador T. Jurado, both of Santa Ana, Calif.

[73] Assignee: Weyerhaeuser Company, Tacoma, Wash.

[21] Appl. No.: 428,509

[22] Filed: Sep. 29, 1982

[51] Int. Cl.[3] ..... A01H 9/00

[52] U.S. Cl. ..... PLT./88

[58] Field of Search ..... Plt./88

*Primary Examiner*—Robert E. Bagwill

*Attorney, Agent, or Firm*—Weyerhaeuser Company

[57] ABSTRACT

A mutation of the Australian Tree Fern, characterized by its slower growth, a more compact habit, and reduced height and width at maturity.

3 Drawing Figures

The present invention relates to a new and distinct dwarf variety of a plant of the family Cyatheaceae and more particularly to a plant of the pecies *Sphaeropteris cooperi* (F. J. Muell.) Tryon (*Alsophila cooperi* F. J. Muell.; *Cyathea cooperi* (F. J. Muell.) Domin), commonly known as Australian tree fern.

This new variety was discovered at Hines Wholesale Nursery, 12621 Jeffery Road, Santa Ana, Calif. The new variety originated as a mutant of cultivated *Sphaeropteris cooperi.* We noted the plant in a group of about 12,000 plants which had been reproduced from spores. The dwarf plant was isolated and observed with other plants of the same age in the block until it was confirmed as being typologically distinct. At this time the main stem tip was removed and reproduced by tissue culture at Santa Rosa Tropicals, Santa Ana, Calif. The buds formed in culture have been divided and recultured, so that several thousand plantings of the new variety have been produced. These have been grown at Hines Wholesale Nursery, Santa Ana, Calif. In all Instances, the descendants of the original plant have retained the same distinguishing characteristics as the original mutant plant, establishing that the variety is stable and true to type.

This new variety has a number of distinguishing characteristics and desirable features which set it off from its parents or any other known *Sphaeropteris cooperi* variety. The crown of fronds is more prostrate and compact and the foliage is denser and more symmetrical. The crown also carries more fronds. There is no indication that the new variety is not as hardy and environmentally tolerant as the standard *Sphaeropteris cooperi.*

The accompanying color photographs serve to illustrate the new plant variety, wherein.

DETAILED PLANT DESCRIPTION p0 Name: *Sphaeropteris cooperi.* Dwarf Australian Tree Fern.

Parentage: A mutation during spore reproduction of a standard variety of *Sphaeropteris cooperi.*

Size: Ultimate height is not known, as no specimen has as yet reached full maturity. Present indications are that full height will not exceed four meters and may be lower (approximately half the height of a standard plant).

Growth habit: Foliage dense and compact. Indications are that full spread will be reached within five years after planting a 24 month-old tree in the landscape.

Fronds: 2-3 pinnate, predominantly 2, wide ovate or triangular. Stipe or stem covered with scales having essentially similar cells throughout and not bristle-tipped.

Sori: Round, between marginn and midrib of pinnules, the indusium absent or, if present, cuplike, globose, or of scales.

Texture: Firm and somewhat hairy.

Appearance: Symmetrical, perfectly shaped and divided, small version of its parents.

Disease and insect resistance: No disease or insect problems have occurred requiring other than normal nursery spraying common to all tree ferns.

Climatic range: Has withstood temperatures ranging from 30° to 103° F. without any harmful effects on the plant. While this specific plant has not been exposed to temperatures lower than 30° F., it derives from plants which are hardy in Zones 9 and 10, where low temperatures range from 20° F. to 30° F.

Color: The frond color, in The Royal Horticultural Society Colour Chart, is under Fan No. 3, Green group, between No. 137B and No. 137C.

Figure 1:
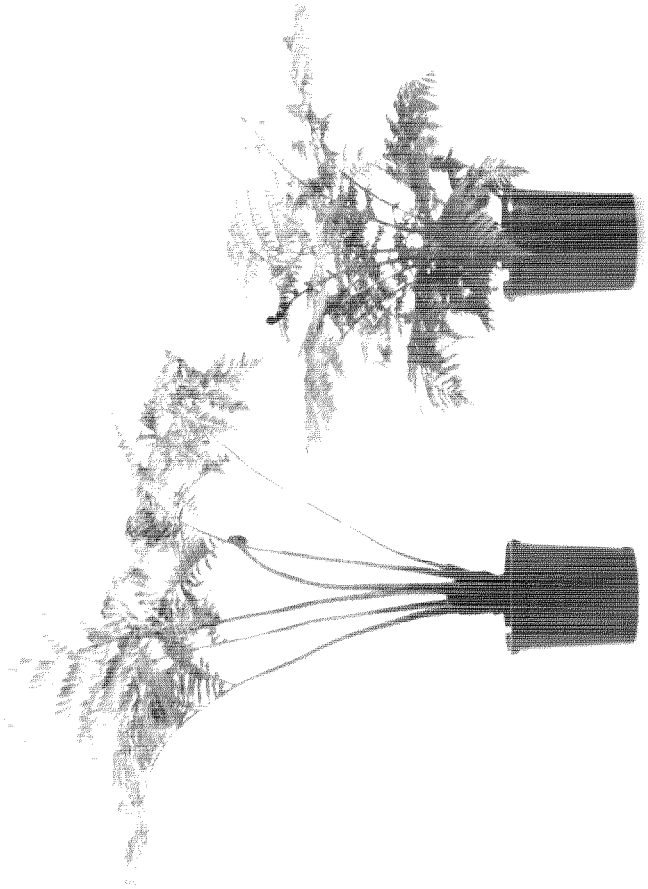
FIG. 1 is a side-by-side comparison of the dwarf variety and a normal plant, each being of approximately 24 months' age.
Figure 2:
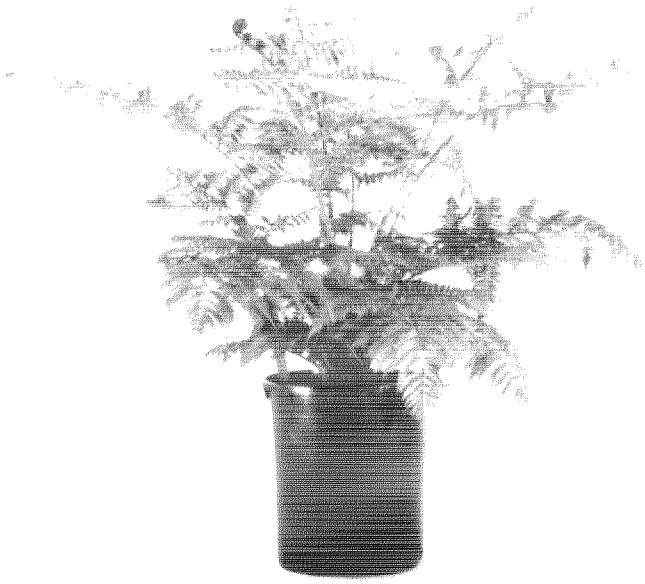
FIG. 2 is a closer view of the new variety, showing its compactness and high foliage density.
Figure 3:
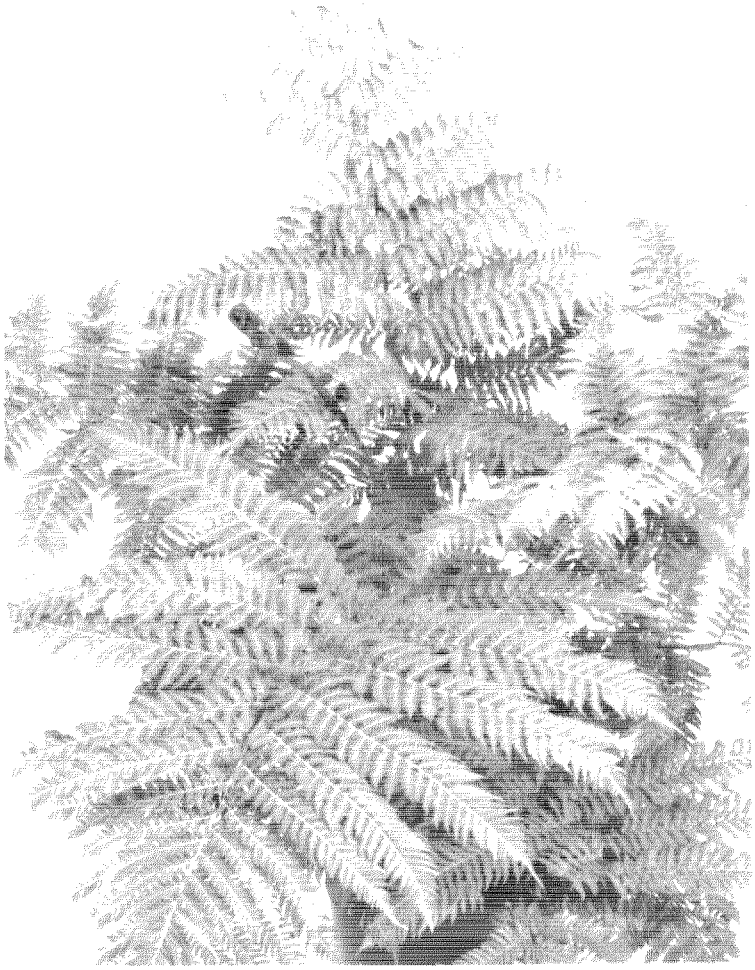
FIG. 3 is a view of the new variety from above, showing the high foliage density.

The specimens shown in the figures are approximately 24 months of age. As a reference scale, the pots are approximately 300 mm high and 280 mm top diameter. The dwarf specimen is approximately 0.7 m high and 1.1 mm in foliage diameter. The normanl plant, shown in FIG. 1, is about 1.3 m high and 1.5 m in foliage diameter.

What is claimed is:

1. A new and distinct plant variety of *Sphaeropteris cooperi* as shown and described, which is principally characterized by its compact and symmetrical growth, its greater foliage density, a higher number of fronds in the crown, and by a mature height and diameter substantially smaller than the standard variety.

* * * * *